United States Patent [19]

Shearer

[11] Patent Number: 6,130,095
[45] Date of Patent: Oct. 10, 2000

[54] METHOD FOR THE MEASUREMENT OF SULFUR COMPOUNDS

[75] Inventor: Randall Lee Shearer, Houston, Tex.

[73] Assignee: Sievers Instruments, Inc., Boulder, Colo.

[21] Appl. No.: 07/824,852

[22] Filed: Jan. 23, 1992

[51] Int. Cl.[7] .................................................. G01N 21/62
[52] U.S. Cl. ........................................... 436/123; 436/161
[58] Field of Search ..................... 436/123, 161, 436/172; 422/52, 98

[56] References Cited

U.S. PATENT DOCUMENTS

| | | | |
|---|---|---|---|
| 3,880,587 | 4/1975 | Szakasits et al. | 436/123 |
| 4,193,963 | 3/1980 | Bruening et al. | 422/52 |
| 4,843,016 | 6/1989 | Fine | 422/52 |

*Primary Examiner*—Lyle A. Alexander
*Attorney, Agent, or Firm*—David Silverstein Andover-IP-Law

[57] ABSTRACT

An improved system for the measurement of sulfur compounds is described. The system comprises an enclosed burner assembly for the conversion of sulfur-containing compounds to sulfur monoxide and subsequent detection of sulfur monoxide by ozone-induced chemiluminescence. The new burner assembly provides higher efficiency for the conversion of sulfur compounds to produce sulfur monoxide than previous flame-based detection systems.

14 Claims, 5 Drawing Sheets

METHOD FOR THE MEASUREMENT OF SULFUR COMPOUNDS

BACKGROUND OF THE INVENTION

Determination of the concentrations and identities of sulfur-containing compounds is an important application in analytical chemistry. The presence of sulfur compounds in crude oils, petroleum feedstocks, and petroleum products is detrimental to the processing of petroleum and can poison and destroy expensive catalysts used in these processes. Sulfur compounds can also impart undesirable tastes and odors in food, flavors, and beverages and therefore routine measurements of the levels of sulfur compounds in a wide range of foods and beverages is performed. Many of the commonly used pesticides and herbicides are sulfur containing compounds and detection of these compounds in water, air, soil and foods is important in protection of the environment and insuring the safety of the consumer. Sulfur gases are a major source of air pollution and acid rain, requiring sensitive monitoring techniques. Many biologically important compounds contain sulfur or are converted to sulfur-containing products as part of analytical measurement techniques such as amino acid sequencing using Edman protein degradation. These examples and numerous other applications highlight the need for sensitive and selective detection of sulfur containing compounds.

For some applications, measurement of the total concentration of sulfur species is sufficient, while in other applications, the identification and quantification of individual sulfur-containing compounds is required. This later application is usually performed using chromatographic techniques including gas chromatography, liquid chromatography, supercritical fluid chromatography and other separation techniques.

Measurement of total sulfur content is usually performed using x-ray fluorescence, combustion of the sample and detection of $SO_2$ by fluorescence or radiometric techniques. The best sensitivity of these techniques are generally in the low parts per million range, while the needs of the petroleum and chemical industries are techniques that can measure total sulfur contents in the low parts per billion range.

Numerous detection systems selective for sulfur-containing compounds have been developed for use with chromatography. Representative of the prior art is the Flame Photometric Detection (FPD), the Hall Electrolytic Conductivity Detector (HECD), the Atomic Emission Detector (AED) and several chemiluminescence-based detectors. The FPD is not well suited for sulfur detection having a non-linear response for sulfur compounds and suffering from quenching of the sulfur response due to the presence of non-sulfur-containing compounds. The HECD is not widely used for sulfur detection and it is difficult to operate and maintain. Both the FPD and HECD have different responses for various sulfur-containing compounds which makes calibration of the detectors difficult and prohibits the use of these detectors for the measurement of total sulfur content of a sample. The AED offers advantages over other sulfur-selective chromatographic detectors; however, the apparatus is expensive and requires highly skilled operators.

An improved system for the measurement of sulfur compounds in air was developed by Benner and Stedman and is described in 61 *Anal. Chem.* 1268–71 (1989). In this system, sulfur compounds are combusted in a hydrogen-rich/air flame to produce sulfur monoxide. The combustion products are collected by means of a quartz sampling probe and transferred to a separate reaction chamber where the gases are mixed with ozone. Sulfur monoxide reacts with ozone to produce electronically excited sulfur dioxide, which relaxes by emission of light (h v) in the blue and ultraviolet region of the spectrum.

Sulfur Compound→SO+other products

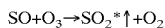

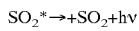

This Sulfur Chemiluminescence Detector (SCD™) has a linear and equimolar response for sulfur compounds and does not suffer from interference or quenching due to the presence of non-sulfur-containing compounds.

A detection system for chromatography based on the SCD technique has been developed by Godec and Johansen and is described in U.S. application Ser. No. 07/759,105 filed Sep. 6, 1991. The chromatography detector employs a conventional flame ionization detector (FID) operated under hydrogen rich conditions as the combustion source for the production of sulfur monoxide. A high purity ceramic probe is positioned in the FID flame and used in conjunction with a vacuum pump to collect approximately 90% of the flame's gases and to transfer the sulfur monoxide to a reaction chamber. Ozone is mixed with the flame gases in the reaction chamber and the emitted light is monitored using a photomultiplier tube. This configuration permits simultaneous monitoring of the FID and SCD detector signals, providing information on both the sulfur components and non-sulfur compounds in a sample.

This SCD technology forms the basis of commercial instruments for use with gas, liquid and supercritical fluid chromatography and provides high sensitivity (<5 pg S/sec), high selectivity (>$10^6$ g S/g C) with no interference or quenching of the sulfur signal from non-sulfur compounds. Despite offering improved performance for sulfur-selective detection in chromatography, the basic FID/SCD detection system has some limitations. A flame ionization detector is required for use of the SCD and the sensitivity and selectivity of the detector is strongly dependent on the flow rates of hydrogen and air to the FID and the position of the ceramic probe in the flame. Adjustment of the position of the probe is therefore required for operation and some degree of skill and training is required for this adjustment. Silicon compounds and other materials such as the bleed from a gas chromatographic column can cause loss in sensitivity of the detector by deposition of materials on and inside the ceramic probe. Finally, many applications require the detection of sulfur compounds at concentrations below the detection limit of the current SCD instrumentation. The need for improved sensitivity, ease of operation, greater utility and elimination of factors which reduce sensitivity has led to the development of an improved system for the measurement of sulfur compounds.

Improved sensitivity of the SCD should be possible. Benner and Stedman have shown using gas phase titration of SO produced in the quartz burner with $NO_2$ that only 0.4% of the sulfur molecules entering the quartz burner are converted to SO. See 61 *Anal. Chem.* 1268–71 (1989). Thermodynamic studies have shown that the concentration of SO can be increased by operation of the combustion under optimum hydrogen and air mixtures. The present invention employs a new ceramic burner assembly which permits operation under conditions which increase the production of sulfur monoxide and improve the sensitivity of the SCD.

SUMMARY OF THE INVENTION

The present invention includes a combustion chamber designed for the increased production of sulfur monoxide from sulfur-containing compounds and improved sensitivity in the detection of sulfur monoxide by ozone-induced chemiluminescence. This improved combustion/detection system can be applied to the measurement of total sulfur content of a sample or used as a detector for gas, liquid and supercritical fluid chromatography.

In the present invention, sulfur-containing compounds in a flowing gas or liquid stream are mixed with a controlled amount of oxygen, air or other chemical oxidizing agent and enters a heated ceramic combustion assembly. A second controlled gas flow rate of a fuel such as hydrogen is introduced into the heated ceramic combustion assembly and mixes with the same sample stream and oxidant stream. The amount of fuel is controlled to be in stoichiometric excess to the amount of oxidant and sample. The temperature of the ceramic combustion assembly is controlled to provide sufficient temperature to initiate ignition of the fuel and oxidant, providing a combustion zone within the ceramic chamber. In the combustion zone, sulfur-containing compounds are converted to sulfur monoxide and other products.

The totality of gaseous products are withdrawn from the ceramic chamber by means of a vacuum pump and transferred to a chemiluminescence reaction chamber where the gases are mixed with ozone. Ozone reacts with sulfur monoxide to produce electronically excited sulfur dioxide ($SO_2^*$) which emits light in the blue and ultraviolet region of the spectrum. The emitted radiation is monitored by means of a photomultiplier tube, photodiode or similar light detection system. An optical filter may be employed to limit the wavelengths of radiation reaching the light detection system or the full spectrum of emitted radiation may be passed to the light detection system. The output of the light detection system is then amplified and electronically processed to produce an analog or digital electronic signal that is proportional to the amount of radiation measured in the chemiluminescence reaction chamber for output to a computer, integrator or other recording device capable of integrating the electronic output signal. The magnitude of the electronic output signal is proportional to the amount of radiation emitted in the chemiluminescence reaction chamber, which is in turn, proportional to the amount of sulfur-containing compounds present in the sample stream.

In certain applications, the components of the sample may be first separated using a chromatographic technique including gas chromatography, supercritical fluid chromatograph or liquid chromatography. For application to gas chromatography, the effluent of the gas chromatography column is mixed with air or oxygen at the inlet of the ceramic chamber. For gas chromatography using capillary columns, the column may be positioned inside the ceramic chamber and an additional flow of an inert gas, such as helium of nitrogen, may be used to help sweep the effluent from the capillary column into the ceramic chamber.

For application to supercritical fluid chromatography, a restrictor comprised of a small inside diameter capillary or one of many available frit restrictors is positioned at the inlet of the ceramic burner to depressurize the supercritical fluid stream. For application to liquid chromatography, the temperature of the ceramic chamber may be operated at a temperature sufficient to cause evaporation of the liquid stream to facilitate combustion of the sample. Alternatively, an additional heated zone may be provided prior to the inlet of the ceramic chamber to permit evaporation of the liquid stream.

For the determination of total sulfur content of a sample, a heated inlet may be installed prior to the ceramic chamber and an external source of an inert gas used to facilitate transport of the sample into the ceramic chamber.

A key element of the present invention is the use of ceramic materials for the combustion of the sample and the production of sulfur monoxide. Construction of similar burner design using quartz or metal components does not appear to provide for production of sulfur monoxide at the levels obtained using the ceramic design. The combination of a ceramic reaction chamber, operation of the reaction chamber under more reducing (fuel-rich) conditions and at reduced pressures provides for significantly higher yield of sulfur monoxide from the combustion of sulfur compounds than is observed in previous quartz burners or detection systems employing a convention flame ionization detector. For example, in one embodiment, the flow rate of hydrogen fuel is approximately 80 mL/min and the flow rate of air is approximately 20 mL/min providing a molar $H_2/O_2$ ratio of about 20:1. In contrast, an air flow rate of 400 mL/min and a hydrogen flow rate of 200 mL\min (molar $H_2/O_2$ ratio= 2.5:1) gives the maximum sensitivity for previous detection systems using flame ionization detector burners. The equilibrium reaction:

$$SO_2+H_2<->SO+H_2O$$

is believed to be important in the chemistry of the SCD. The use of the ceramic burner assembly permits operation at higher hydrogen concentrations which results in a shift of the equilibrium to the right and results in an increase in the concentrations of SO formed from the combustion of sulfur-containing compounds. External heating of the ceramic combustion assembly provides for initiation and sustaining combustion of hydrogen and air even at flow rates which are outside of the flammability limits for hydrogen in air.

This new ceramic burner design is also less susceptible to contamination from silicon compounds and other materials which cause loss in the sensitivity in the quartz and FID burner systems.

Operation of the ceramic chamber at reduced pressures also provides for increased sensitivity in the detection of sulfur monoxide by ozone-induced chemiluminescence by reducing non-radiative collisional quenching of the emitting species ($SO_2^*$) in the chemiluminescence reaction chamber. In the quartz and FID burner systems, the chemiluminescence reaction chamber must be operated at higher pressures.

DESCRIPTION OF THE PREFERRED EMBODIMENT

Figure 1:
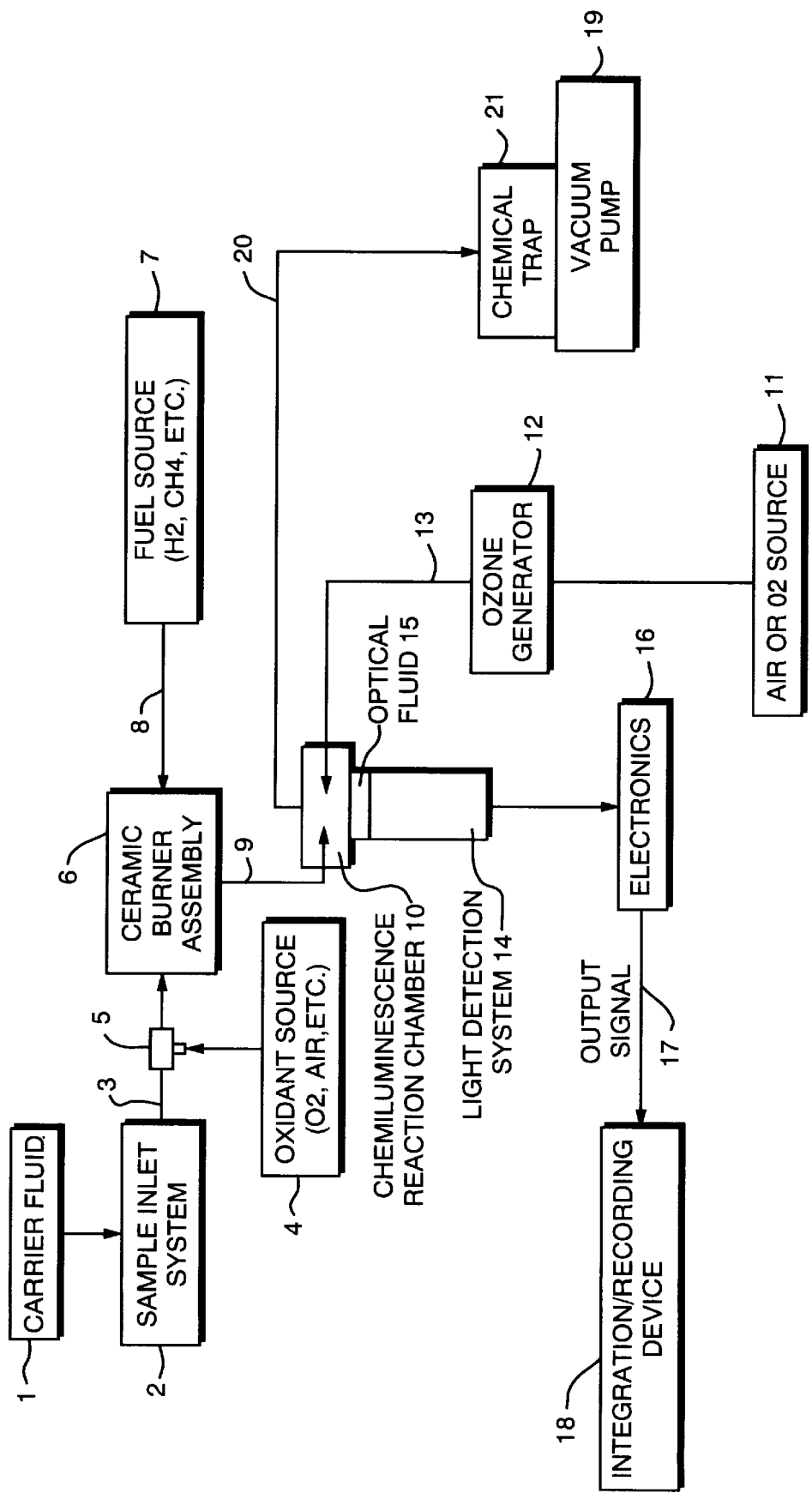
FIG. 1 shows a block diagram of the improved sulfur chemiluminescence detection system.

FIG. 1 shows a generalized schematic of the improved sulfur chemiluminescence detection system. The carrier fluid 1 and the sample inlet 2 are representative of the various technique that can be used for introduction of the sample into the detection system. For example, in one embodiment, the carrier fluid 1 is a carrier gas and the sample inlet system 2 is a gas chromatograph. In a second embodiment, the carrier fluid 1 is a source of supercritical fluid, such as supercritical $CO_2$ and the sample inlet system 2 is a supercritical fluid chromatograph. In a third embodiment, the carrier fluid 1 is a solvent reservoir and the sample inlet system 2 is a liquid chromatograph. In a fourth embodiment, the carrier fluid 1 is a inert gas supply and the sample inlet system 2 is a vaporization chamber.

For all of these embodiments, the effluent 3 of the sample inlet system 2 is a gaseous stream containing sulfur compounds. An oxidant is delivered from the oxidant supply 4 and mixed with the effluent 3 via a mixing tee 5 and enters the ceramic burner assembly 6. A supply of fuel is delivered from the fuel source 7 via the fuel inlet line 8 to the ceramic burner assembly 6. Combustion of the fuel, oxidant and sample in the ceramic burner assembly results in the production of sulfur monoxide and other products which are transferred via the ceramic burner assembly outlet 9 to a chemiluminescence reaction chamber 10. Air or oxygen is supplied from an air or oxygen source 11 to an ozone generator 12 and flows into the chemiluminescence reaction chamber 10 via the ozone inlet line 13. Reaction of the ceramic burner assembly effluent with ozone in chemiluminescence reaction chamber 10 results in the emission of light which is detected by the light detection system 14 comprised of a photomultiplier tube, photodiode or array of photodiodes or any other similar light detection system. An optical filter 15 may be used to limit the wavelengths of radiation that impinge upon the light detection system 14. The signal from the light detection system 14 is processed using suitable electronics 16 to supply an output signal 17 to a integration and recording device 18. A vacuum pump 19 is used to evacuate the chemiluminescence reaction chamber 10 via the outlet line 20. Excess ozone and other reactive gases are removed using the chemical trap 21.

Figure 2:
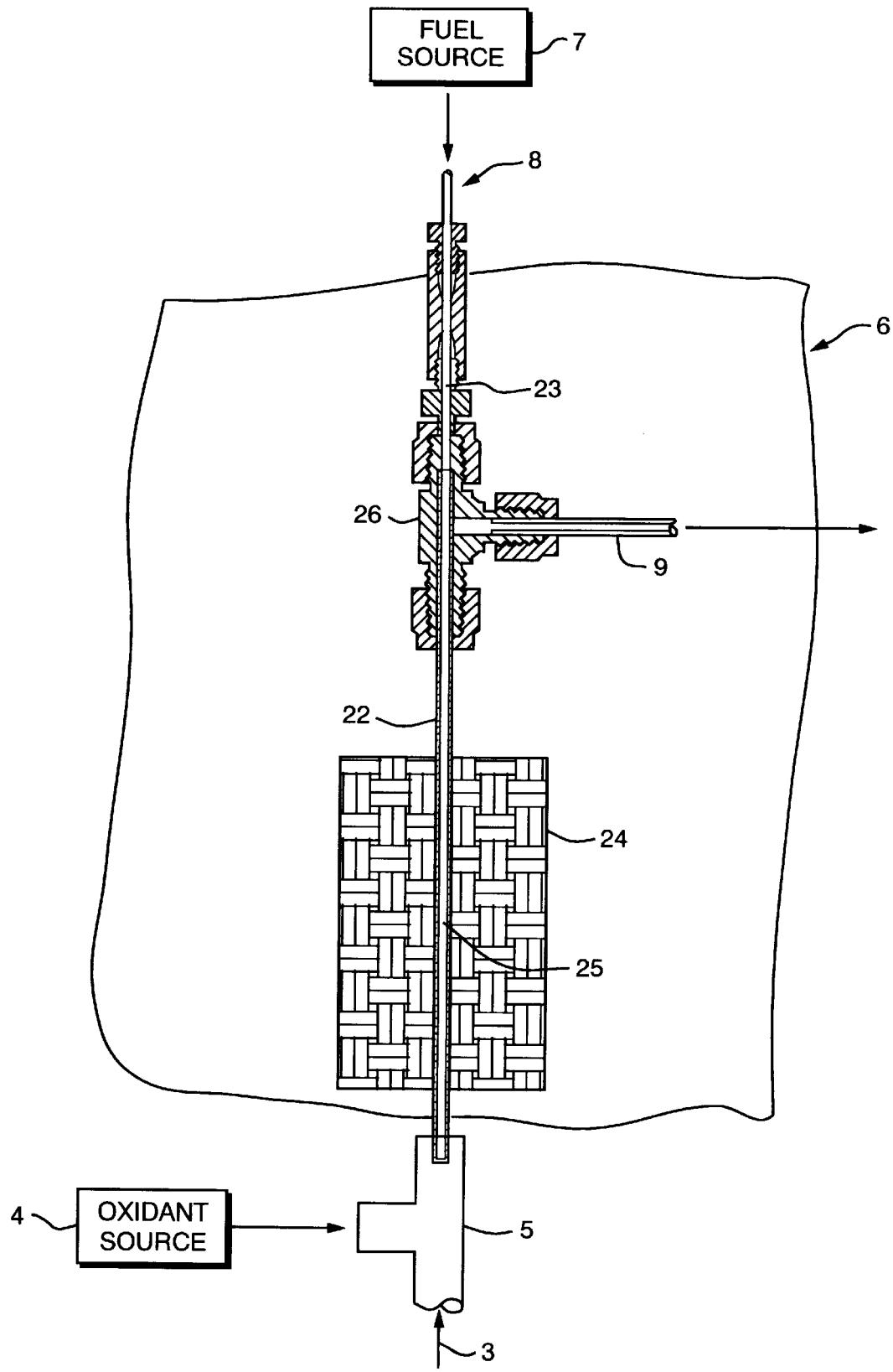
FIG. 2 shows a detailed diagram of the ceramic burner assembly.

A more detailed schematic of the ceramic burner assembly is shown in FIG. 2. In one preferred embodiment, the sample inlet system effluent 3 is mixed with air or oxygen from and oxidant source 4 in mixing tee 5. The ceramic burner assembly 6 is comprised of a outer ceramic tube 22 having an outside diameter of approximately 1/8" and an inside diameter of greater than 1/16". A second, inner ceramic tube 23, having an outside diameter of approximately 1/16" (.050 inch) is positioned inside of the outer ceramic tube 22, the positioning being approximately centered radially in the outer tube providing a small gap between the outside wall of the inner ceramic tube 23 and the inside wall of the outer ceramic tube 22. The outer ceramic tube 22 is connected to the mixing tee 5 and the inner ceramic tube 23 is connected to the fuel source 7, via the fuel inlet line 8. An external heater 24 is positioned around the outer ceramic tube 22 and the temperature of the ceramic tubes is controlled by a temperature controller (not shown). A combustion zone 25 is created in the region at the outlet of the inner ceramic tub 23 where the fuel from the fuel source 7 contacts the oxidant from the oxidant source 4. The outlet of the outer ceramic tube 22 is connected to a tee 26 which is also connected to the burner assembly outlet 9.

In operation, the products from the combustion zone 25 are continually drawn by the vacuum pump 19 through the gap between the inner and outer ceramic tubes, through the tee 26 and into the burner assembly outlet 9 for transport to the chemiluminescence reaction chamber 10. In this manner, the combustion products contact a relatively large region of heated ceramic which promotes or assists in the production of sulfur monoxide and reduces or minimizes the formation of other sulfur-containing products such as $H_2S$ or $SO_2$. The reason that the ceramic furnace promotes or assists in the production of sulfur monoxide is not entirely clear, but it may be a result of the alumina in the ceramic making additional oxygen available.

The following examples are presented by way of illustration and in no way limit the present invention. Specifically, other sample inlet system means may be employed to include other chromatographic systems, including liquid and supercritical fluid chromatography and non-chromatographic systems for introduction of gaseous, liquid or solid samples containing sulfur compounds.

Figure 3:
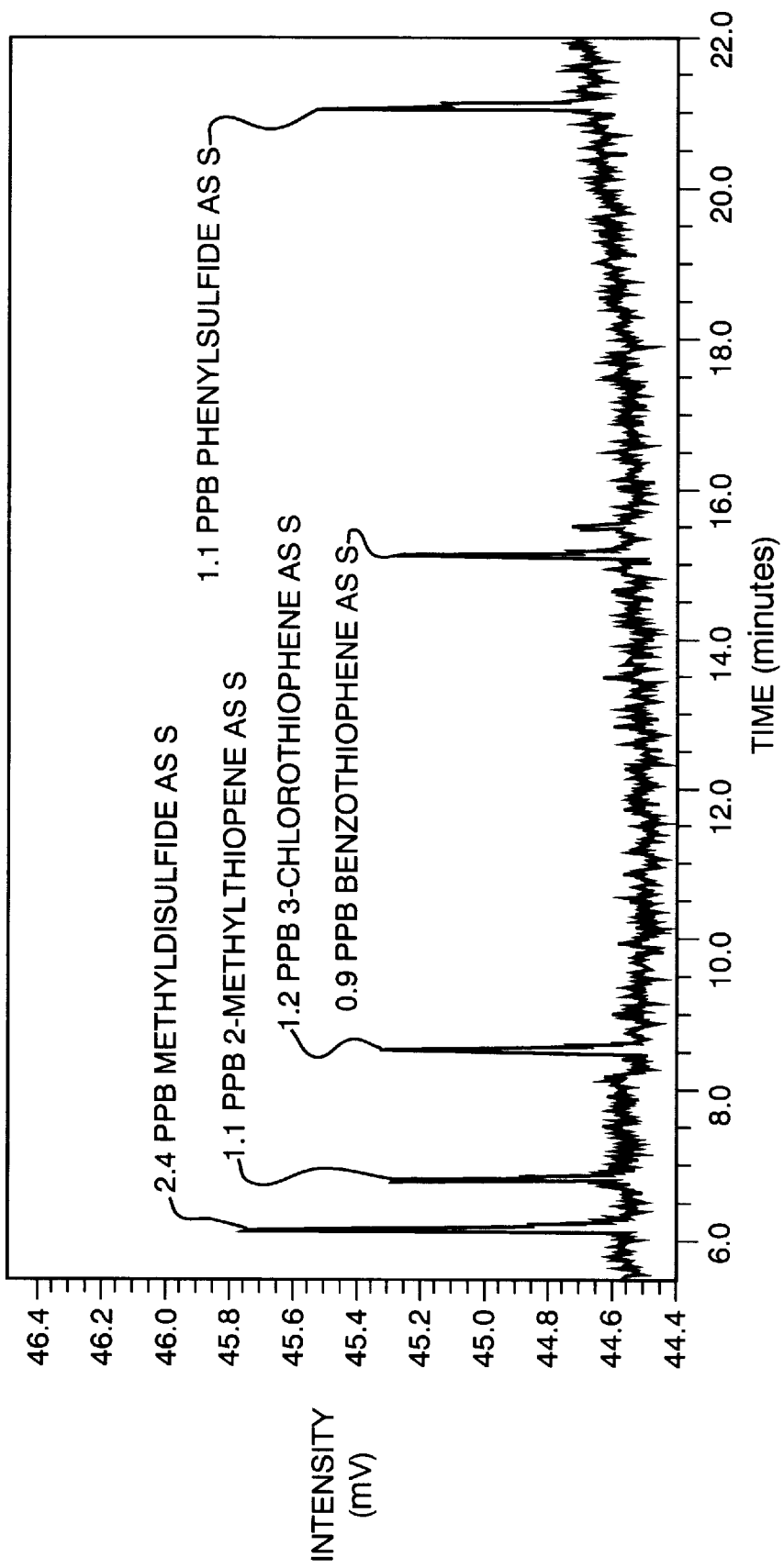
FIG. 3 shows an example of the sensitive and selective detection of sulfur compounds using the detection system in conjunction with gas chromatography.

An example of the improved sensitivity for the detection of sulfur-containing compounds using gas chromatography as the sample inlet system is shown in FIG. 3. In this example, a 1 microliter sample of a solution containing five sulfur compounds in a hydrocarbon solvent (hexane) was analyzed by gas chromatography and detected using the ceramic burner assembly/SCD. The concentration of the sulfur compounds is approximately 1 nanogram of compounds per milliliter of solvent. Based on the molecular formula and molecular weight of the compounds, approximately 0.7 picograms of sulfur is eluting from the gas chromatographic column for each component, entering the ceramic burner assembly and being detected. As shown in FIG. 3, the height of the chromatographic peaks is significantly larger than the baseline noise and no detector response is observed for the hexane solvent, even though 0.7 mg of hexane is entering the detection system.

FIG. 3 also illustrates the eqimolar response of the present invention for sulfur compounds. The response of the detector is the same for equal amounts of sulfur from different sulfur-containing compounds, greatly simplifying calibration and quantification of the system. Calibration can be performed using a single sulfur-containing compounds where other sulfur-selective detection systems such as the flame photometric detector require calibration for each individual sulfur compound to be measured.

Figure 4:
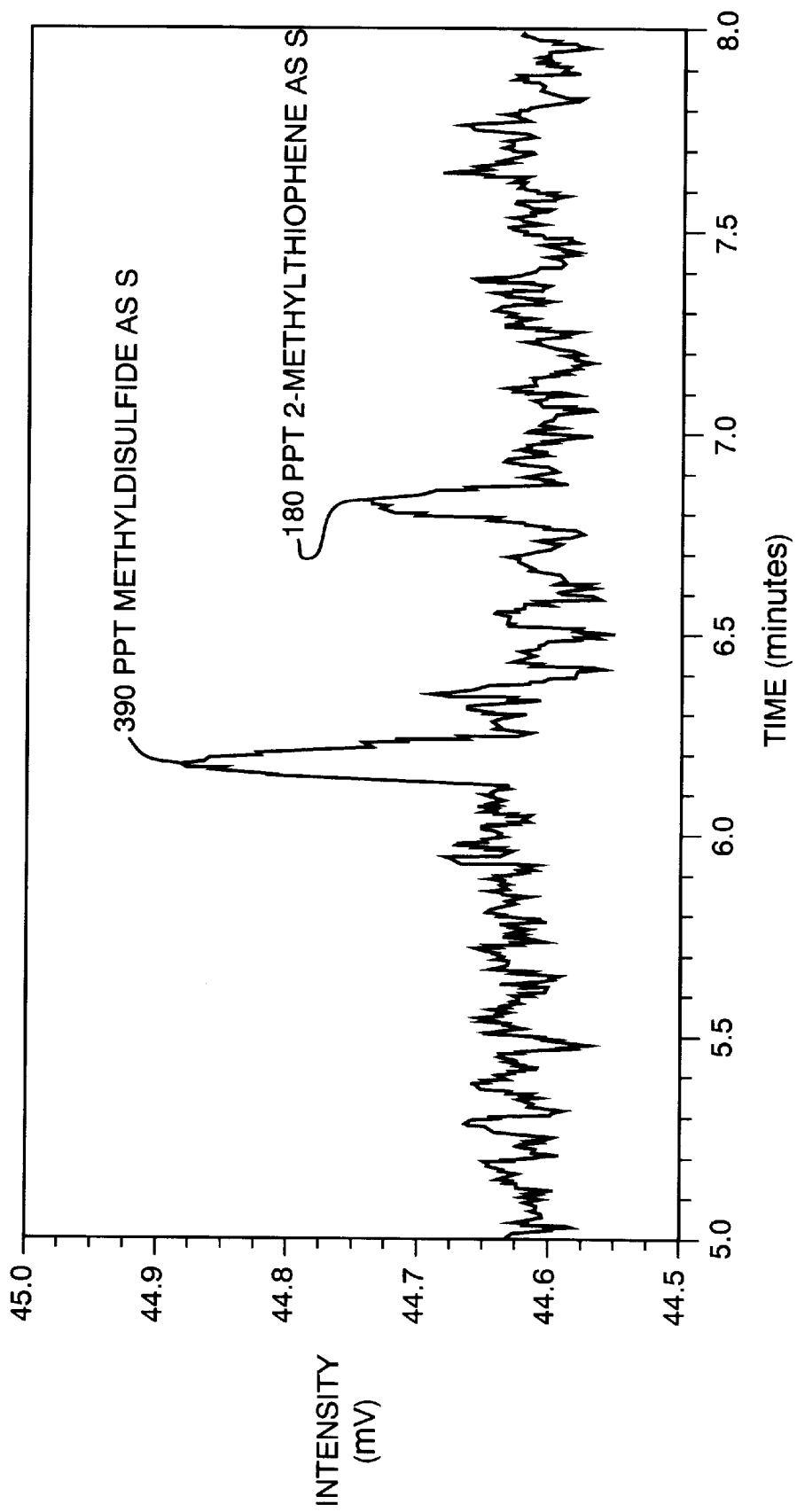
FIG. 4. shows an example of the detection of parts per trillion levels of sulfur using the detection system in conjunction with gas chromatography.

Detection of sulfur-containing compounds at even lower concentrations using the current invention is shown in FIG. 4. For this example, a gas chromatograph was employed as the sample inlet system and a 1 microliter sample of solution containing two sulfur compounds was analyzed. The concentration of sulfur compounds in this solution is 570 picograms of dimethyldisulfide and 550 picograms of 2-methylthiophene per milliliter of hexane solvent. As shown in FIG. 4, chromatographic peaks corresponding to 390 femtograms of sulfur for dimethyldisulfide and 180 femtograms of sulfur for 2-methylthiophene can be readily distinguished from the baseline noise.

The detection limit for chromatographic systems is commonly described as the amount of material which produces a chromatographic peak whose height divided by the width of the peak at one half of the peak height is equal to three times the peak to peak baseline noise. From the chromatogram shown in FIG. 4 the detection limit for these sulfur compounds is approximately 0.02 picograms of sulfur per second. In this embodiment, the present invention is a significant improvement over the prior art; detection limits for sulfur detection by ozone-induced chemiluminescence using other burner components and designs have been reported to be 0.4 to 5 picograms sulfur per second. Thus the present invention is at least an order of magnitude more sensitive than the prior art.

Figure 5:
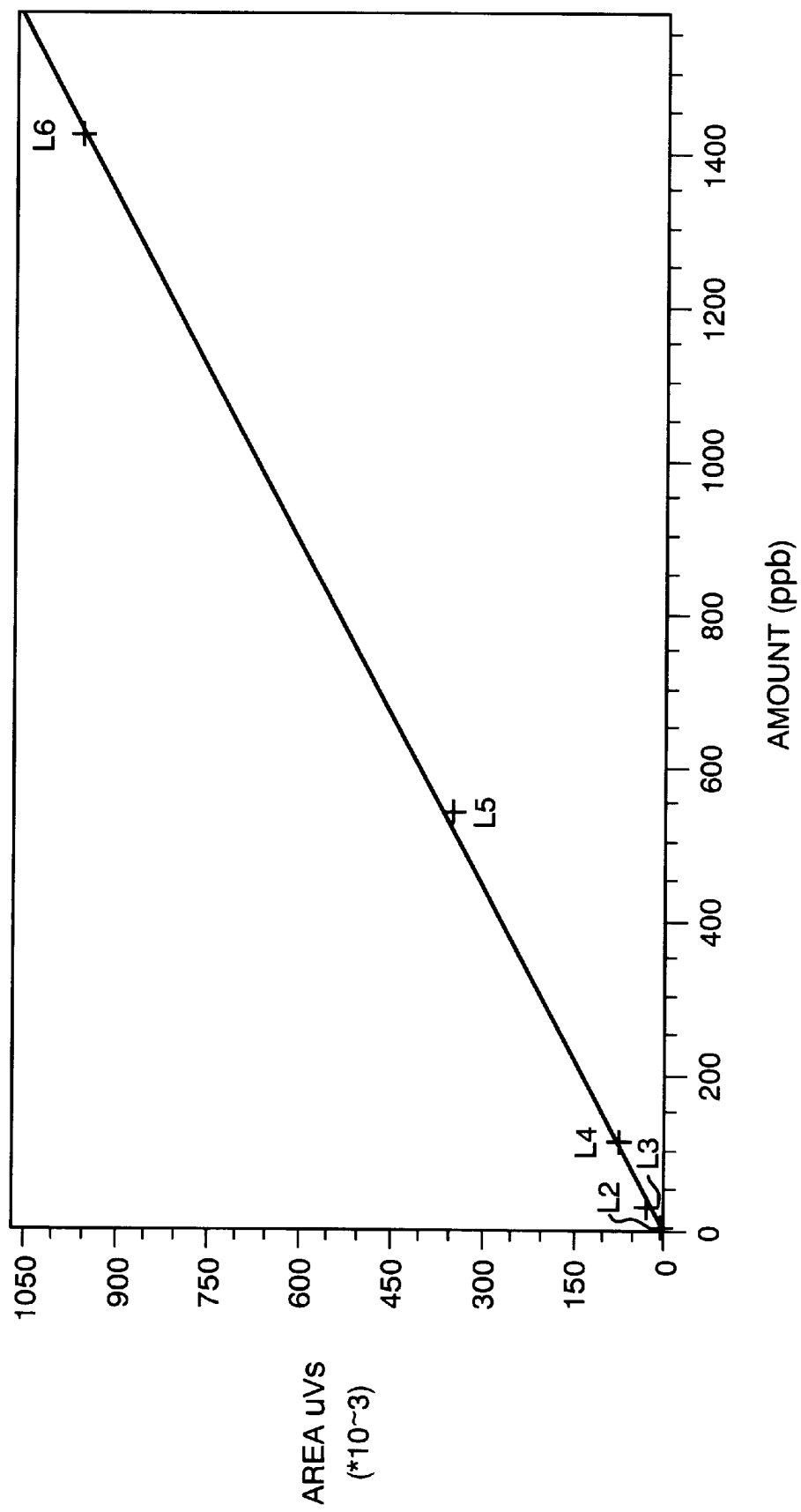
FIG. 5. shows an illustration of the linear response of the detection system as a function of the concentration of sulfur-containing compounds in a sample.

An important feature of the detection of sulfur compounds by formation of sulfur monoxide and ozone-induced chemiluminescence is the linearity of the detector response as a function of sulfur compound amount or concentration. The present invention retains this linear response as indicated in FIG. 5 for methyl ethyl sulfide. Analysis of six samples containing different concentrations of methyl ethyl sulfide was performed over a range from approximately 1.5 nanogram of compound per milliliters to approximately 1400 nanogram of compound per milliliter. As shown in FIG. 5, the response of the detector is linear over at least three orders of magnitude.

It is therefore to be understood from the foregoing that various modifications and changes may be made in the process and apparatus of the present invention as herein set forth and described without departing from the spirit and scope thereof, as defined by the following claims.

What is claimed is:

1. A method for measuring sulfur compounds in a sample, comprising oxidizing the sample in a ceramic furnace to produce sulfur monoxide; reacting the sulfur monoxide with ozone; and measuring the radiation resulting from the reaction of sulfur monoxide with ozone to determine the sulfur content in the sample.

2. The method of claim 1, wherein said sample is converted into a gas stream prior to being oxidized.

3. The method of claim 1, wherein at least a portion of said sample is chromatographically separated prior to being oxidized.

4. The method of claim 3, wherein said chromatographic separation is by gas chromatography.

5. The method of claim 3, wherein said chromatographic separation is by liquid chromatography.

6. The method of claim 3, wherein said chromatographic separation is by supercritical fluid chromatography.

7. The method of claim 1, wherein at least a portion of said sample is mixed with a separate fuel before being oxidized.

8. The method of claim 7, wherein said ceramic furnace is heated.

9. The method of claim 8, wherein said ceramic furnace is heated to a temperature between approximately 600° C. and 1000° C.

10. The method of claim 7, wherein the amount of such mixed fuel is such that less than all the fuel is consumed by the oxidation.

11. The method of claim 7, wherein said ceramic furnace includes a first ceramic tube for the passage of the sample and a second ceramic tube co-axial with the first ceramic tube for the passage of the fuel, the first and second ceramic tubes being in fluid communication with one another and the oxidation taking place at the area where they communicate.

12. The method of claim 11, wherein the second ceramic tube has a smaller diameter than, and is positioned at least partially inside of, the first ceramic tube, and opens into the interior of the first ceramic tube, so that the sample oxidizes where the fuel flows out of the second tube and into the interior of the first tube, and then the oxidized sample flows through the first tube between the first tube wall and second tube wall.

13. The method of claim 1, wherein said sulfur monoxide and ozone are mixed in a reaction chamber at a pressure less than atmospheric.

14. The method of claim 1, wherein said measuring of radiation is by a chemiluminescence detector.

* * * * *